United States Patent [19]

Desbois

[11] Patent Number: 4,554,381

[45] Date of Patent: * Nov. 19, 1985

[54] PROCESS FOR SULFONYLATION OF HALOBENZENES

[75] Inventor: Michel Desbois, Rillieux, France

[73] Assignee: Rhone-Poulenc Specialites Chimiques, Courbevoie, France

[ * ] Notice: The portion of the term of this patent subsequent to Nov. 12, 2002 has been disclaimed.

[21] Appl. No.: 392,885

[22] Filed: Jun. 28, 1982

[30] Foreign Application Priority Data

Jan. 21, 1982 [FR] France ............................... 82 00879

[51] Int. Cl.$^4$ ........................................... C07C 147/06
[52] U.S. Cl. .................................. 568/34; 260/465 F; 260/465 G; 562/429; 568/28; 568/30; 568/31; 568/33
[58] Field of Search ....................... 568/28, 33, 34, 31, 568/30; 562/429; 260/465 F, 465 G

[56] References Cited

U.S. PATENT DOCUMENTS

| | | | |
|---|---|---|---|
| T970,006 | 5/1978 | Rose | 260/591 |
| 2,273,922 | 2/1942 | Benning et al. | 260/649 |
| 2,275,312 | 3/1942 | Tinker et al. | 260/515 |
| 2,372,562 | 3/1945 | Emerson | 260/592 |
| 2,735,868 | 2/1956 | Frevel et al. | 260/592 |
| 2,781,402 | 2/1957 | Chadwick | 568/34 |
| 2,974,172 | 3/1961 | Luvisi | 260/592 |
| 3,187,057 | 6/1965 | Peter et al. | 260/651 |
| 3,387,035 | 6/1968 | Gray et al. | 260/591 |
| 3,732,307 | 5/1973 | Middleton | 260/566 B |
| 3,883,594 | 5/1975 | Schmerling | 260/592 |
| 3,953,400 | 4/1976 | Dahl | 260/47 |
| 3,967,949 | 7/1976 | Benefiel et al. | 71/76 |
| 4,178,460 | 12/1979 | Berkelhammer et al. | 562/426 |
| 4,207,266 | 6/1980 | Opie | 260/651 F |
| 4,276,226 | 6/1981 | Clement et al. | 260/410.5 |

FOREIGN PATENT DOCUMENTS

| | | |
|---|---|---|
| 43861 | 1/1982 | European Pat. Off. . |
| 0069598 | 1/1983 | European Pat. Off. . |
| 876690 | 5/1953 | Fed. Rep. of Germany . |
| 1645153 | 10/1970 | Fed. Rep. of Germany . |
| 2451037 | 4/1976 | Fed. Rep. of Germany . |
| 1567806 | 4/1969 | France . |
| 7721091 | 7/1977 | France . |
| 135756 | 10/1979 | Japan . |
| 1164817 | 9/1969 | United Kingdom . |
| 2030158 | 4/1980 | United Kingdom . |
| 2045760 | 11/1980 | United Kingdom . |

OTHER PUBLICATIONS

March, J., "Advanced Organic Chemistry," 465–466, 2nd ed., McGraw-Hill, (1977).
Yasui, K. et al., Chemical Abstract, 92:215144K, (1980).
Morrison and Boyd, "Organic Chemistry," 341–342, Allyn and Bacon Inc., Boston, Mass. (3rd ed., 1973).
Buu-Hoi, et al., *J. Org. Chem.*, V. 26, pp. 2401–2402 (1961).
L. Yagupolskii, et al., *Chem. Abstracts*, 61:8217 (1964).
V. Boiko et al., *Chem. Abstracts*, 87:134226 h (1977).
G. Olah, Friedel-Crafts and Related Reactions, III, Part II, Chapter XL (1964).

*Primary Examiner*—Donald G. Daus
*Assistant Examiner*—Mary E. Ceperley
*Attorney, Agent, or Firm*—Herbert F. Schwartz; James F. Haley, Jr.; Paul H. Ginsburg

[57] ABSTRACT

A process for sulfonylation of halobenzenes, in which a halobenzene is reacted with a sulfonic acid, a precursor or a derivative thereof in the presence of boron trifluoride in an amount such that the absolute pressure of boron trifluoride within the reaction vessel exceeds 1 bar, and in the presence of hydrofluoric acid as a solvent. The resultant products are useful as intermediates in the synthesis of compounds having a phytosanitary (e.g., herbicidal) or pharmaceutical activity.

7 Claims, No Drawings

PROCESS FOR SULFONYLATION OF HALOBENZENES

The instant invention is directed to a process for sulfonylation of halobenzenes. The invention is directed more particularly to the preparation of sulfones by a sulfonylation reaction, i.e., by reaction of the corresponding halobenzene and a sulfonic acid, a precursor or a derivative thereof.

Sulfonylation reactions in the presence of catalysts such as $AlCl_3$, $FeCl_3$ and $SbCl_5$ in an organic solvent medium are known (Olah, *Friedel-Crafts and Related Reactions* III, Part II, Interscience Publishers, p. 1319 et seq. (1964)); in this process, the substrate can also be the solvent.

These processes have drawbacks which can be attributed above all to the nature of the catalyst. It is necessary to use a significant quantity of catalyst. More than one mole of catalyst, such as aluminum chloride, must be used per mole of substrate, because the sulfonyl group of the reagent or of the resultant sulfone forms a 1:1 molar complex with aluminum chloride, The large quantity of, e.g., $AlCl_3$ requires a correspondingly large quantity of water for its elimination. Moreover, its recovery on an industrial scale is impossible.

The instant invention is directed to a process for the sulfonylation of halobenzenes, characterized in that a halobenzene is reacted with a sulfonic acid, a precursor or a derivative thereof in the presence of boron trifluoride in an amount such that the absolute pressure of the boron trifluoride in the reaction vessel exceeds 1 bar, and in the presence of hydrofluoric acid as a solvent.

The process of the invention is that much more surprising inasmuch as it is stated in the prior art (Olah, supra, page 1338) that boron trifluoride is inactive as a catalyst in sulfonylation reactions.

Within the scope of this invention, the term halobenzene refers to both the compounds themselves and to derivatives thereof with one or a plurality of substituents on the benzene nucleus.

More particularly, the invention is directed to the reaction of compounds having the formula:

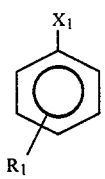

(I)

wherein $X_1$ represents chlorine, bromine, iodine or fluorine and $R_1$ represents at least one element or moiety selected from the group consisting of hydrogen, OH, Cl, Br, I, F, alkyl and alkoxy radicals having from 1 to 6 carbon atoms, and phenyl and phenoxy radicals substituted by at least one group more deactivating than $X_1$.

The phenyl and phenoxy radicals $R_1$ must be substituted by a group or groups more deactivating than the $X_1$ group so that the sulfonylation reaction takes place on the benzene nucleus bearing the $X_1$ group. Otherwise, acylation would occur on the phenyl or phenoxy radical. Examples of groups more deactivating than the $X_1$ group include $NO_2$, COOH, CN and keto groups.

One can cite as examples of compounds of Formula I the following: chlorobenzene; fluorobenzene; bromobenzene; iodobenzene; o-, m- and p-fluorotoluene; o-, m- and p-dichlorobenzene; o-, m- and p-fluorophenol; o-, m- and p-fluorochlorobenzene; o-, m- and p-fluoroanisole; o-, m- and p-difluorobenzene; o-, m- and p-chlorotoluene; o-, m- and p-chloroanisole; 4-trifluoromethyl-4'-chlorobiphenyl; and 4-trifluoromethyl-2,4'-dichlorodiphenyl oxide, as well as the chlorinated, brominated and iodinated analogues of the above compounds.

Within the scope of this invention, the terms sulfonic acid, precursors and derivatives thereof refer to all the sulfonylation reagents well known in the prior art.

According to a particular embodiment of the invention, the sulfonic acid, its precursor or derivative is of the general formula:

$$R_2SO_2X_2 \quad (II)$$

wherein $R_2$ represents an aliphatic or aromatic radical and $X_2$ represents halogen, OH, $OR_3$, $NH_2$, $NHR_4$ or $NR_5R_6$, wherein each of $R_3$, $R_4$, $R_5$, and $R_6$ is an aromatic or aliphatic radical.

The invention is well suited in particular to the use of a compound of Formula II wherein $R_2$ represents an alkyl, phenyl, alkylphenyl or phenylalkyl radical or a phenyl radical bearing at least one substituent such as, for example, halogen, $NO_2$, CN, $NH_2$, COOH, $CF_3$, $CCl_3$, or $CBr_3$.

Examples of such compounds include paratoluenesulfonyl chloride, benzenesulfonyl chloride, paratoluenesulfonic acid, benzenesulfonic acid, methanesulfonyl chloride, ethanesulfonyl chloride, orthotoluenesulfonyl chloride, 2,4-dimethylbenzenesulfonyl chloride, metanitrobenzenesulfonyl chloride, 2-methoxybenzenesulfonyl chloride, parachlorobenzenesulfonyl chloride, parahydroxybenzenesulfonyl fluoride and parabenzylbenzenesulfonyl chloride.

The process according to the invention is preferably carried out by using an amount of hydrofluoric acid such that the molar ratio of the hydrofluoric acid to the halobenzene is between 5 and 50. Even more preferably, this ratio is between 10 and 30.

The hydrofluoric acid used is preferably anhydrous. The use of an aqueous hydrofluoric acid would result in a useless consumption of boron trifluoride in the form of a complex of HF, $BF_3$ and $H_2O$ ($H_3O^+BF_4^-$).

The halobenzene and the sulfonic acid, its precursor or derivative are used in substantially equimolar amounts. A slight excess of the halobenzene may, however, be desirable.

More particularly, it is preferred to use an amount of boron trifluoride such that the absolute pressure of $BF_3$ within the reaction vessel is between 6 and 20 bars. A pressure in excess of 20 bars is not excluded from the scope of the invention; however, it does not provide any particular benefit. The more the pressure is increased, the greater the increase in the rate of the reaction. The pressure will therefore be adjusted to maximize the efficiency of the process.

The process of the invention is preferably carried out at a temperature between −20° C. and 150° C. The reaction times are generally between a few minutes and several hours.

The phenyl sulfones obtained according to the process of the invention have the general formula:

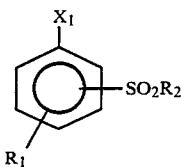

wherein $X_1$, $R_1$ and $R_2$ have the same meaning as above.

The position of the $SO_2R_2$ group with respect to the $X_1$ and $R_1$ groups is in conformity with the substitution rules well known to the organic chemist.

The sulfones produced by the process of the invention are useful, in particular, as intermediates in the synthesis of compounds having a pharmaceutical or phytosanitary (e.g., herbicidal) activity.

The following are examples of compounds that can be prepared by the process of the invention: 4-fluoro-4′-methyldiphenyl sulfone; 4-fluorodiphenyl sulfone; 4-fluoro-3-methyldiphenyl sulfone; 4-fluoro-3,4′-dimethyldiphenyl sulfone; 4-chloro-4′-methyldiphenyl sulfone; 4-fluorophenylmethyl sulfone; 4-nitro-4′-bromodiphenyl sulfone; 4-fluorophenylethyl sulfone; 4-fluoro-2-methyldiphenyl sulfone; 4-fluoro-2-chloro-4′-methyldiphenyl sulfone; 5-fluoro-2-hydroxy-4′-chlorodiphenyl sulfone; 3-chloro-4-methoxydiphenyl sulfone; and 2-chloro-4,4′-dihydroxydiphenyl sulfone.

In order to disclose more clearly the nature of the present invention, the following examples illustrating specific embodiments of the invention are given. It should be understood, however, that this is done solely by way of example and is intended neither to delineate the scope of the invention nor limit the ambit of the appended claims.

EXAMPLE 1

Into a 250 ml stainless steel reactor equipped with a magnetic stirrer system, 100 ml of anhydrous HF, 38.1 g (0.2 mole) of p-toluenesulfonyl chloride and 19.2 g (0.2 mole) of fluorobenzene were introduced at around 0° C. The reactor was closed and gaseous boron trifluoride ($BF_3$) introduced until the pressure was constant at 10 bars. The reaction was then allowed to proceed with stirring at ambient temperature for 23 hours. Following reaction, the reactor was decompressed to atmospheric pressure, then the reaction mixture poured over 200 g of crushed ice. The resultant heterogeneous mixture was extracted three times with 200 ml of methylene chloride. The organic phases were washed three times with 200 ml of water, once with 200 ml of an aqueous 3% potassium hydroxide solution, and twice with 200 ml of water. The organic phase as dried over magnesium sulfate and the solvent eliminated by distillation under reduced pressure. 49.5 g (yield: 99%) of 4-fluoro-4′-methyldiphenyl sulfone was recovered.

EXAMPLE 2

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| Benzenesulfonyl chloride | 35.5 g (0.2 mole) |
| Boron trifluoride | 6 bars at 20° C. |
| Temperature | 40° C. |
| Duration | 1 hour |

41 g (yield: 87%) of 4-fluorodiphenyl sulfone having a purity of 99.5% was recovered.

EXAMPLE 3

The reaction was carried out as in Example 1 with the following compounds and under the following conditions:

| | |
|---|---|
| Anhydrous hydrofluoric acid | 100 g |
| o-fluorotoluene | 22 g (0.2 mole) |
| Benzenesulfonyl chloride | 35.5 g (0.2 mole) |
| Boron trifluoride | 10 bars at 20° C. |
| Temperature | 20° C. |
| Duration | 4 hours |

46 g (yield: 92%) of 4-fluoro-3-methyldiphenyl sulfone having a purity of 97% was recovered.

EXAMPLE 4

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| p-toluenesulfonic acid | 34.4 g (0.2 mole) |
| Boron trifluoride | 10 bars at 20° C. |
| Temperature | 80° C. |
| Duration | 6 hours |

44 g (yield: 88%) of 4-fluoro-4′-methyldiphenyl sulfone was recovered.

EXAMPLE 5

The reaction was carried out as in Example 1 with the following compounds and under the following conditions:

| | |
|---|---|
| Anhydrous hydrofluoric acid | 100 g |
| o-fluorotoluene | 22 g (0.2 mole) |
| p-toluenesulfonic acid | 34.4 g (0.2 mole) |
| Boron trifluoride | 10 bars at 20° C. |
| Temperature | 80° C. |
| Duration | 4 hours |

43.9 g (yield: 83%) of 4-fluoro-3-methyldiphenyl sulfone having a purity of 80% was recovered.

EXAMPLE 6

The reaction was carried out as in Example 1 with the following compounds and under the following conditions:

| | |
|---|---|
| Anhydrous hydrofluoric acid | 100 g |
| Bromobenzene | 31.4 g (0.2 mole) |
| Benzenesulfonyl chloride | 35.3 g (0.2 mole) |
| Boron trifluoride | 6 bars at 20° C. |
| Temperature | 20° C. |
| Duration | 4 hours |

51.6 g (yield: 87%) of 4-bromodiphenyl sulfone having a purity of 85% was recovered.

EXAMPLE 7

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| Methanesulfonyl chloride | 34.4 g (0.3 mole) |
| Boron trifluoride | 10 bars at 20° C. |
| Temperature | 100° C. |
| Duration | 5 hours |

16 g (yield: 46%) of 4-fluorophenylmethyl sulfone having a purity of 70% was recovered.

EXAMPLE 8

The reaction was carried out as in Example 1 with the following compounds and under the following conditions:

| | |
|---|---|
| Anhydrous hydrofluoric acid | 100 g |
| o-fluoroanisole | 25.8 g (0.2 mole) |
| p-toluenesulfonyl chloride | 38.1 g (0.2 mole) |
| Boron trifluoride | 10 bars at 20° C. |
| Temperature | 20° C. |
| Duration | 1 hour |

55 g (yield: 97%) of 3-fluoro-4-methoxy-4'-methyldiphenyl sulfone having a purity of 92% was recovered.

EXAMPLE 9

The reaction was carried out as in Example 1 with the following compounds and under the following conditions:

| | |
|---|---|
| Anhydrous hydrofluoric acid | 100 g |
| 3-fluoro-1-chlorobenzene | 13 g (0.1 mole) |
| Benzenesulfonic acid | 15.8 g (0.1 mole) |
| Boron trifluoride | 15 bars at 20° C. |
| Temperature | 120° C. |
| Duration | 24 hours |

19.8 g (yield: 70%) of a mixture of 4-fluoro-2-chlorodiphenyl sulfone and 2-fluoro-4-chlorodiphenyl sulfone was recovered.

EXAMPLE 10

The reaction was carried out as in Example 1 with the following compounds and under the following conditions:

| | |
|---|---|
| Anhydrous hydrofluoric acid | 100 g |
| 3-fluorophenol | 11.2 g (0.1 mole) |
| p-toluenesulfonic acid | 17.2 g (0.1 mole) |
| Boron trifluoride | 10 bars at 20° C. |
| Temperature | 20° C. |
| Duration | 4 hours |

25.3 g (yield: 95%) of a mixture of 2-fluoro-4'-methyl-4-hydroxydiphenyl sulfone and of 4-fluoro-4'-methyl-2-hydroxydiphenyl sulfone was recovered. In this example, the washing with an aqueous 3% potassium hydroxide solution was eliminated in order not to extract the phenol that was formed.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

I claim:

1. A process for the preparation of phenyl sulfones having the formula:

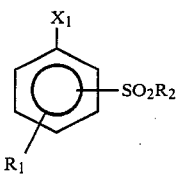

said process comprising reacting a halobenzene having the formula:

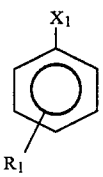     (I)

in a reaction vessel with a sulfonic acid, a precursor or a derivative thereof having the formula:

$$R_2SO_2X_2 \qquad (II)$$

in the presence of boron trifluoride in an amount such that the absolute pressure of boron trifluoride within the reaction vessel exceeds 1 bar and in the presence of hydrofluoric acid as a solvent; wherein $X_1$ is Cl, Br, I, or F;

$R_1$ is at least one element or moiety selected from the group consisting of hydrogen, OH, Cl, Br, I, F, alkyl and alkoxy radicals having from 1 to 6 carbon atoms, and phenyl and phenoxy radicals substituted by at least one group more deactivating than $X_1$;

$X_2$ is a halogen, OH, $OR_3$, $NH_2$, $NHR_4$, or $NR_5R_6$, wherein each of $R_3$, $R_4$, $R_5$, and $R_6$ is an aromatic or aliphatic radical; and $R_2$ is an aliphatic or aromatic radical.

2. A process according to claim 1 wherein $R_2$ is alkyl, phenyl, alkylphenyl, phenylalkyl, or phenyl bearing at least one halogen, $NO_2$, CN, $NH_2$, COOH, $CF_3$, $CCl_3$, or $CBr_3$ substituent.

3. A process according to claim 1 wherein an amount of hydrofluoric acid is used such that the molar ratio of hydrofluoric acid to the compound of formula I is between 5 and 50.

4. A process according to claim 1 wherein the hydrofluoric acid used is anhydrous hydrofluoric acid.

5. A process according to claim 1 wherein the compounds of formulas I and II are used in substantially equimolar amounts.

6. A process according to claim 1 wherein an amount of boron trifluoride is used such that the absolute pressure of boron trifluoride within the reaction vessel is between 6 and 20 bars.

7. A process according to claim 1 wherein the reaction temperature is between −20° C. and 150° C.

* * * * *